US007345079B2

(12) United States Patent
Teng et al.

(10) Patent No.: US 7,345,079 B2
(45) Date of Patent: Mar. 18, 2008

(54) TREATMENT OF DISORDER RELATED TO LOW CYCLIC GMP LEVELS

(75) Inventors: Che-Ming Teng, Taipei (TW); Fang-Yu Lee, Tachia Taichung (TW); Sheng-Chu Kuo, Taichung (TW)

(73) Assignee: Yung Shin Pharmaceuticals Industrial Co., Ltd, Taichung (TW)

( * ) Notice: Subject to any disclaimer, the term of this patent is extended or adjusted under 35 U.S.C. 154(b) by 499 days.

(21) Appl. No.: 10/325,990

(22) Filed: Dec. 19, 2002

(65) Prior Publication Data
US 2003/0220385 A1 Nov. 27, 2003

Related U.S. Application Data

(60) Provisional application No. 60/344,207, filed on Dec. 26, 2001.

(51) Int. Cl.
*A01N 43/56* (2006.01)
*A61K 31/45* (2006.01)
(52) U.S. Cl. ...................................................... 514/406
(58) Field of Classification Search ................. 514/406
See application file for complete search history.

(56) References Cited

U.S. PATENT DOCUMENTS 5,574,168 A * 11/1996 Kuo et al. ............... 548/360.5
6,162,819 A * 12/2000 Schindler et al. ........... 514/405
6,387,942 B2 * 5/2002 Teng et al. ................. 514/414
6,518,294 B2 * 2/2003 Teng et al. ................. 514/403

FOREIGN PATENT DOCUMENTS

CN 1214339 4/1999
EP 0 908 456 A1 4/1999
JP 02255970 10/1990

OTHER PUBLICATIONS

Osol A. [Editor]. "Chapter 27: Structure-Activity Relationship and Drug Design". Remington's Pharmaceutical Sciences (Sixteenth Edition). Mack Publishing, 1980. pp. 420-435.*
Mayer et al., "cGMP Signalling Beyond Nitricoxide", Trends in Pharmacological Sciences 22:546-548, 2001.
Tulis et al., "YC-1, a Benzyl Indazole derivative, Stimulates Vascular cGMP and Inhibits Neointima Formation", Biochemical and Biophysical Research Communications 279:646-652, 2000.
Yu et al., "cGMP-Elevating Agents Suppress Proliferation of Vascular Smooth Muscle Cells by Inhibiting the Activation of Epidermal Growth Factor Signaling Pathway", Circulation 95:1269-1277, 1997, XP002243240.
Yu et al., "Inhibition of Platelet Function by A02131-1, a Novel Inhibitor of cGMP-Specific Phosphodiesterase, In Vitro and In Vivo", Blood 87:3758-3767, 1996, XP-002056082.

* cited by examiner

*Primary Examiner*—Ardin H. Marschel
*Assistant Examiner*—Leslie A Royds
(74) *Attorney, Agent, or Firm*—Howrey LLP; Viola T. Kung

(57) ABSTRACT

Disclosed in this invention is a method of treating a disorder associated with low cGMP levels. The method includes administering to a subject in need thereof an effective amount of a compound having a pyrazolyl core, a first aryl group bonded to 3-C of the pyrazolyl core, and a second aryl group fused at 4-C and 5-C of the pyrazolyl core. Also disclosed are pharmaceutical compositions containing these compounds.

2 Claims, No Drawings

TREATMENT OF DISORDER RELATED TO LOW CYCLIC GMP LEVELS

CROSS REFERENCE TO RELATED APPLICATIONS

Pursuant to 35 USC § 119(e), this application claims the benefit of prior U.S. provisional application No. 60/344,207, filed Dec. 26, 2001.

BACKGROUND OF THE INVENTION

Cyclic 3',5'-guanosine monophosphate (cGMP), an intracellular secondary messenger, is converted from GTP by guanylate cyclase and broken down to GMP by phosphodiesterases (PDEs), e.g., PDE 5. It plays an important role in various physiological functions. For example, it relaxes the vascular smooth muscle in organs such as heart, lung, and penis. GMP deficiency causes various disorders, e.g., coronary heart disease, hypertension, and impotence.

As cGMP is hydrolyzed by PDEs, disorders related to cGMP deficiency caused by high PDE activity can be treated by administering a PDE inhibitor to increase the cGMP levels.

SUMMARY OF THE INVENTION

The present invention includes to a method of treating a disorder associated with low cGMP levels by administering a PDE inhibitor that is a fused pyrazolyl compound.

Formula (I) below encompasses a set of fused pyrazolyl compounds that can be used to practice the method of this invention:

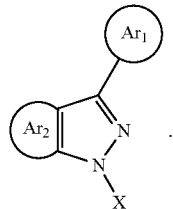

(I)

Each of these compounds includes a pyrazolyl core and two aryl groups. The first aryl group $Ar_1$ is phenyl, thienyl, furyl, or pyrrolyl, optionally substituted at a ring carbon atom with halo, alkyl, alkoxy, carboxyl, (alkoxy)carbonyl, (alkylthio)carbonyl, aminocarbonyl, hydroxyalkyl, (alkoxy)alkyl, amino, aminoalkyl, thioalkyl, (alkylthio)alkyl, or alkylenedioxy. The second aryl group is phenyl, thienyl, furyl, or pyrrolyl, substituted at a ring carbon with halo, alkyl, alkoxy, carboxyl, (alkoxy)carbonyl, (alkylthio)carbonyl, aminocarbonyl, hydroxyalkyl, (alkoxy)alkyl, amino, aminoalkyl, thioalkyl, (alkylthio)alkyl, or alkylenedioxy. X, attached to 1-N (optionally via an alkylene, alkenylene, or alkynylene linker; not shown), is hydrogen, halo, carboxyl, alkoxycarbonyl, thiocarbonyl, aminocarbonyl, hydroxyalkyl, alkoxyalkyl, amino, aminoalkyl, thioalkyl, or aryl; aryl refers to phenyl, thienyl, furyl, or pyrrolyl, optionally substituted with halo, alkyl, alkoxy, carboxyl, (alkoxy)carbonyl, thioalkyl, (alkylthio)carbonyl, aminocarbonyl, hydroxyalkyl, (alkoxy)alkyl, amino, aminoalkyl, (alkylthio)alkyl, or alkylenedioxy.

A subset of the compounds include those in which the first aryl group is phenyl or furyl, optionally substituted with alkyl, alkoxy, hydroxyalkyl, (alkoxy)alkyl, aminoalkyl, thioalkyl, or (alkylthio)alkyl; those in which the first aryl group is furyl, connected to 3-C of the pyrazolyl core at its 2'-C and optionally substituted (e.g., at 5'-C) with alkyl, alkoxy, hydroxyalkyl, (alkoxy)alkyl, aminoalkyl, thioalkyl, or (alkylthio)alkyl; those in which the second aryl group is phenyl or thienyl, substituted with halo, alkyl, alkoxy, carboxyl, (alkoxy)carbonyl, (alkylthio)carbonyl, aminocarbonyl, hydroxyalkyl, (alkoxy)alkyl, amino, aminoalkyl, thioalkyl, (alkylthio)alkyl, or alkylenedioxy; and those in which the second aryl group is phenyl substituted at 5-C and 6-C, together, with methylenedioxo, or at 6-C with halo, alkyl, alkoxy, hydroxyalkyl, (alkoxy)alkyl, amino, aminoalkyl, thioalkyl, or (alkylthio)alkyl.

Formula (I) also encompasses another set of fused pyrazolyl compounds that also can be used to practice the method of this invention. The first aryl group $Ar_1$ is phenyl, thienyl, furyl, or pyrrolyl substituted at a ring carbon with halo, alkyl, alkoxy, carboxyl, thioalkyl, (alkoxy)carbonyl, (alkylthio)carbonyl, aminocarbonyl, (alkoxy)alkyl, amino, aminoalkyl, (alkylthio)alkyl, or alkylenedioxy. The second aryl group $Ar_2$ is phenyl, thienyl, furyl, or pyrrolyl, optionally substituted at a ring carbon atom with halo, alkyl, alkoxy, carboxyl, (alkoxy)carbonyl, (alkylthio)carbonyl, aminocarbonyl, hydroxyalkyl, (alkoxy)alkyl, amino, aminoalkyl, thioalkyl, (alkylthio)alkyl, or alkylenedioxy. X is the same as defined above. Also as described above, X is attached to 1-N, either directly or via an alkylene, alkenylene, or alkynylene linker.

A subset of the compounds includes those in which the first aryl group is phenyl or furyl, substituted with alkyl, (alkoxy)alkyl, aminoalkyl, or (alkylthio)alkyl; those in which the first aryl group is furyl connected to 3-C of the pyrazolyl core and substituted, e.g., at 5'-C, with alkyl, (alkoxy)alkyl, aminoalkyl, or (alkylthio)alkyl; and those in which the second aryl group is phenyl or thienyl, optionally substituted with halo, alkyl, alkoxy, carboxyl, (alkoxy)carbonyl, (alkylthio)carbonyl, aminocarbonyl, hydroxyalkyl, (alkoxy)alkyl, amino, aminoalkyl, thioalkyl, (alkylthio)alkyl, or alkylenedioxy.

The terms "alkyl," the prefix "alk" (e.g., as in alkoxy), and the suffix "-alkyl" (e.g., as in hydroxyalkyl) used herein refer to $C_{1-18}$, linear or branched. The terms "alkylene," "alkenylene," and "alkynylene" refer to divalent alkyl, alkene, and alkyne groups, respectively. Unless otherwise defined, all technical and scientific terms used herein have the same meaning as commonly understood by one of ordinary skill in the art to which this invention belongs.

Examples of the compounds described above include 1-benzyl-3-(5'-hydroxymethyl-2'-furyl)-6-fluoroindazole, 1-benzyl-3-(5'-hydroxymethyl-2'-furyl)-6-methylindazole, 1-benzyl-3-(5'-hydroxymethyl-2'-furyl)-6-methoxyindazole, 1-benzyl-3-(5'-hydroxymethyl-2'-furyl)-5,6-methylenedioxoindazole, and 1-benzyl-3-(5'-methoxymethyl-2'-furyl)indazole. The structure of 1-benzyl-3-(5'- hydroxymethyl-2'-furyl)-5,6-methylenedioxoindazole is shown below, with the atoms in the aryl rings numbered:

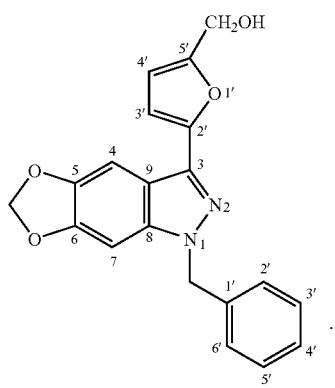

For brevity, the fused pyrazolyl compounds described above include their pharmaceutically acceptable salts and produgs, if applicable. Such a salt can be formed between a negatively charged ionic group in a fused pyrazolyl compound (e.g., carbonate) and a positively charged counterion (e.g., sodium). Likewise, a positively charged ionic group in a fused pyrazolyl compound (e.g., ammonium) can also form a salt with a negatively charged counterion (e.g., chloride). Examples of such salts include the hydrochloride salt of 1-benzyl-3-(5'-aminomethyl-2'-furyl)-5,6-methylenediox-oindazole and the sodium salt of 1-benzyl-3-(5'-carboxyl-2'-furyl)-5,6-methylenedioxo indazole. Examples of prodrugs include esters and other pharmaceutically acceptable derivatives, which, upon administration to a subject, are capable of providing fused pyrazolyl compounds described above.

A fused pyrazolyl compound to be used to practice the method of this invention is formulated into a pharmaceutical composition prior to its use in treating a disorder associated with low cGMP levels. Thus, also within the scope of the invention is a pharmaceutical composition that contains such a fused pyrazolyl compound and a pharmaceutically acceptable carrier for use in treating a disorder associated with low cGMP levels.

The invention also relates to using one of the fused pyrazolyl compounds described above for the manufacture of a medicament for treating a disorder associated with low cGMP levels.

Details of several embodiments of this invention are set forth in the description below. Other features, objects, and advantages of this invention will be apparent from the following description and from the claims.

DETAILED DESCRIPTION OF THE INVENTION

This invention relates to use of a fused pyrazolyl compound to treat a disorder related to low cGMP levels caused by high PDE activity.

The fused pyrazolyl compound can be synthesized as follows: An arylcarbonyl chloride, e.g., benzoyl chloride, is coupled with another aryl group-containing compound containing at least a hydrogen atom on the aryl group, e.g., trifluoromethylbenzene, to form an aryl ketone (e.g., trifluoromethylphenylphenylketone), the two aryl groups of which (e.g., phenyl and phenyl) respectively correspond to Ar$_1$ and Ar$_2$ in Formula (I) or (II). The aryl aryl ketone is then reacted with a hydrazine (e.g., benzylhydrazine) to form a hydrazone, which is subsequently catalytically converted to a fused pyrazolyl compound. The fused pyrazolyl compound thus obtained has an aryl group directly connected to 3-C and another aryl group fused at 4-C and 5-C of the pyrazolyl core. Derivatives of the fused pyrazolyl compound can be obtained by further modification.

The following scheme depicts synthesis of 1-benzyl-3-(5'-hydroxymethyl-2'-furyl)-6-methoxyindazole (detailed description provided in Example 1 below):

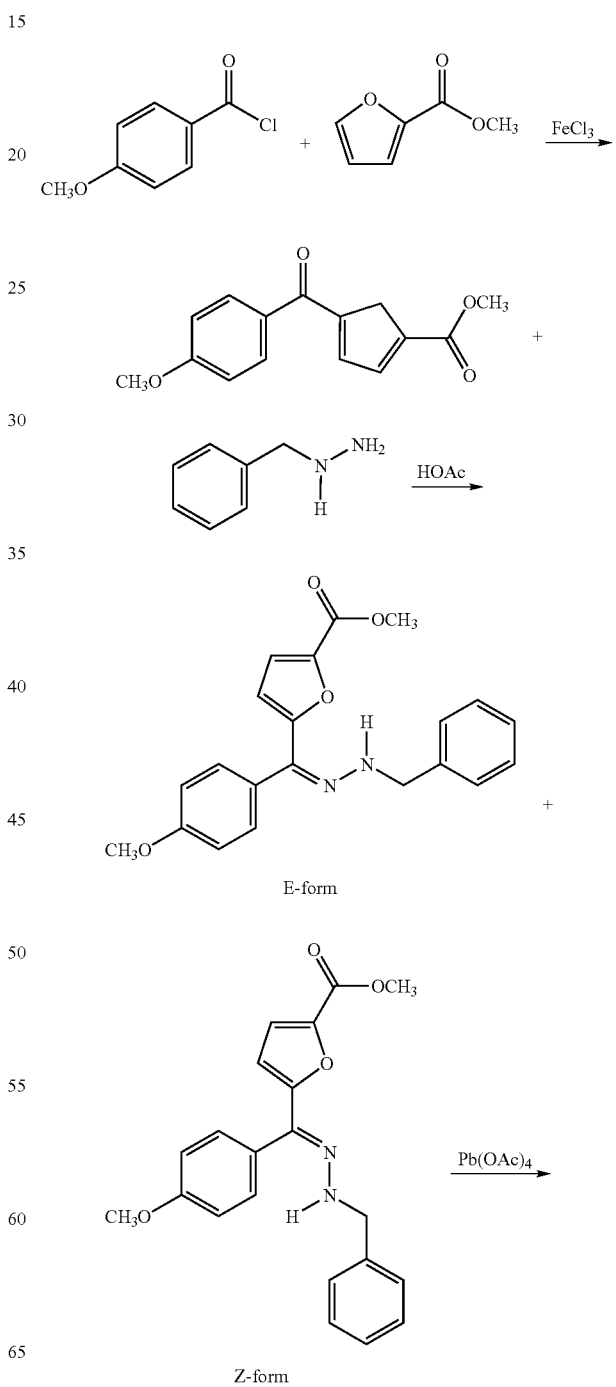

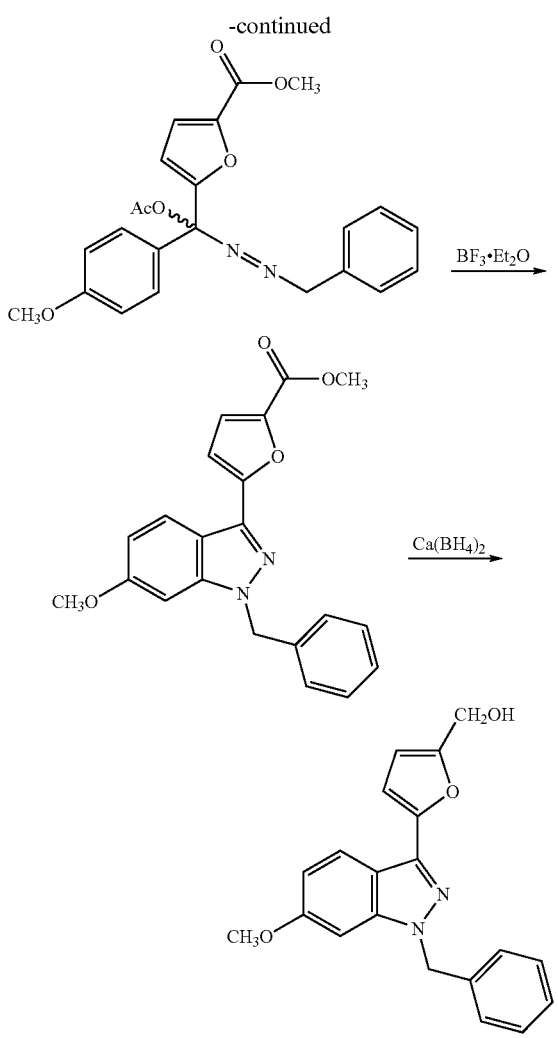

The same synthetic scheme can be employed to synthesize other compounds that also can be used to practice the method of this invention, e.g., 1-benzyl-3-(5'-hydroxymethyl-2'-furyl)-6-fluoroindazole, 1-benzyl-3-(5'-hydroxymethyl-2'-furyl)-6-methylindazole, 1-benzyl-3-(5'-hydroxymethyl-2'-furyl)-5,6-methylenedioxoindazole, and 1-benzyl-3-(5'-methoxymethyl-2'-furyl)indazole. Descriptions of the synthesis of these exemplary compounds are provided in Examples 2, 3, 4, and 5 below. Derivatives of these compounds can be obtained by using as reactants a mono or multi-substituted benzoyl chloride (other than 4-methoxybenzoyl chloride as shown in the above scheme), a mono or multi-substituted 2-furoate (other than methyl-2-furoate as shown in the above scheme), and a mono or multi-substituted benzylhydrazone (instead of benzylhydrazone as shown in the above scheme).

3-Phenyl-indazole compounds can be prepared by following the synthetic scheme shown above except that benzophenone, optionally mono- or multi-substituted, is used, instead of 2-furyl phenyl ketone. As an initial step, benzophenone is oxidized with $CrO_3$ to form benzoylbenzoic acid. The benzoylbenzoic acid is then reacted with ethanol to form ethyl benzoylbenzoate, which is then converted into 3-phenylindazole via a series of reactions (analogous to those shown in the scheme above). If necessary, 3-phenyl-indazole can be converted to its derivatives by further modification.

Fused pyrazolyl compounds containing a thienopyrazole moiety can also be prepared by following the synthetic method shown in the scheme above, except that 2-thienyl aryl ketone, instead of 2-furyl phenyl ketone, is used. The mono- or multi-substitutents, if any, of the thienopyrazolyl compounds thus obtained, can be modified to give additional thienopyrazolyl compounds.

A fused pyrazolyl compound or its salt in an effective amount is formulated into a pharmaceutical composition before being administered to a subject in need of treatment of a disorder associated with low cGMP levels (e.g., cardiovascular diseases such as coronary heart disease and hypertension, or impotence). "An effective amount" refers to the amount of the compound which is required to confer a therapeutic effect on the treated subject. The interrelationship of dosages for animals and humans (based on milligrams per square meter of body surface) is described by Freireich et al., Cancer Chemother. Rep., 1966, 50: 219. The body surface area may be approximately determined from the height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, and the possibility of co-usage with other therapeutic treatments including use of other agents that increase the level of cGMP. Examples of pharmaceutically acceptable carriers include colloidal silicon dioxide, magnesium stearate, cellulose, sodium lauryl sulfate, and D&C Yellow # 10.

The pharmaceutical composition may be administered via a parenteral route, e.g., topically, subcutaneously, intraperitoneally, intramuscularly, and intravenously. Examples of parenteral dosage forms include aqueous solutions of the active compound, in an isotonic saline, 5% glucose, or any other well known pharmaceutically acceptable carriers. Solubilizing agents, such as cyclodextrins, or other solubilizing agents well known to those familiar with the art, can also be included in the pharmaceutical composition.

A fused pyrazolyl compound to be used to practice the method of the invention can be formulated into dosage forms for other routes of administration (e.g., orally, mucosally, or percutaneously) utilizing well known methods. The pharmaceutical composition can be formulated, for example, in dosage forms for oral administration in a capsule, a gel seal, or a tablet. Capsules may comprise any well known pharmaceutically acceptable material such as gelatin or cellulose derivatives. Tablets may be formulated in accordance with the conventional procedure by compressing mixtures of the active compounds, a solid carrier, and a lubricant. Examples of solid carriers include starch and sugar bentonite. The compound can also be administered in a form of a hard shell tablet or capsule containing, for example, lactose or mannitol as a binder, a conventional filler, and a tableting agent.

A suitable in vitro assay can be used to preliminarily evaluate the effect of a fused pyrazolyl compound on inhibiting a PDE, which hydrolyzes cGMP. For example, platelets are washed, suspended in a buffer, and disrupted by sonication to obtain a solution containing a PDE. A compound to be tested and cGMP (a substrate for the PDE) are added to the solution. *Ophiophagus hannah* snake venom is subsequently added to remove the phosphate in 5'-GMP (converted from cGMP by the PDE) to form uncharged guanosine. An ion-exchange resin is used to remove the remaining cGMP. The cGMP-free solution is then centrifuged, and an aliquot of the supernatant is taken for quantification of the uncharged guanosine in a liquid scintillation counter. Activity of the PDE is evaluated based on the amount of the uncharged guanosine. In vivo screening can be performed by following procedures well known in the art.

Without further elaboration, it is believed that one skilled in the art can, based on the description herein, utilize the present invention to its fullest extent. All publications recited herein are hereby incorporated by reference in their entirety. The following specific examples, which describe synthesis and biological testing of various fused pyrazolyl compounds to be used in the method of the present invention, are therefore, to be construed as merely illustrative, and not limitative of the remainder of the disclosure in any way whatsoever.

EXAMPLE 1

Synthesis of 1-benzyl-3-(5'-hydroxymethyl-2'-furyl)-6-methoxyindazole (Compound 1)

0.42 g of anhydrous ferric chloride and 35.8 g of 4-methoxybenzoyl chloride were dissolved in 40 mL $CCl_4$. To the solution was added dropwise 25.22 g of methyl-2-furoate over 10 minutes. The solution was then heated under reflux for 36 hours and, after cooling, mixed with 120 mL of water. The mixture thus obtained was stirred for 1 hour and then allowed to sit until it separated into two layers and a precipitate. The water layer (on top) and the precipitate were extracted with chloroform. The chloroform extract was dried over anhydrous magnesium sulfate and then filtered. The solvent of the filtrate was removed under a reduced pressure to give a residue which was recrystallized from isopropanol to afford 18.5 g of 4-methoxyphenyl 5'-methoxycarbonyl-2'-furyl ketone in a 44% yield.

6.25 g of the just-prepared ketone was dissolved in 60 mL of methanol. To the solution were added 9.0 g of benzylhydrazine and 0.5 mL of acetic acid. The solution thus obtained was heated under reflux until the reaction was completed. After cooling, the solvent was removed to obtain a residue. The residue was dissolved in chloroform, washed subsequently with a dilute HCl solution and water, dried over anhydrous magnesium sulfate, and then filtered. The solvent of the filtrate was removed to give 7.8 g of 5'-methoxycarbonyl-2'-furyl 4-methoxyphenyl ketone benzylhydrazone.

All of the 5'-methoxycarbonyl-2'-furyl 4-methoxyphenyl ketone benzylhydrazone was dissolved in 100 mL of dichloromethane. The solution thus obtained was added dropwise to 40 mL dichloromethane solution containing 28.2 g $Pb(OAc)_4$. The solution was allowed to react at 30±2° C. for 30 minutes, and then mixed with 122 mL of $BF_3 \cdot Et_2O$ (containing 47% of $BF_3$). The mixture was heated under reflux for 30 minutes and then poured into 1000 mL of ice water to terminate the reaction. The mixture thus obtained separated into two phases, i.e., an organic phase and an aqueous phase. The organic layer (the lower phase) was separated, washed sequentially with water and a 10% sodium carbonate solution, neutralized by water wash, dried over anhydrous magnesium sulfate, and concentrated under vacuum to give an oily crude product. Ethanol was then added to the crude product, and the mixture was allowed to stand overnight during which a solid precipitated. The precipitate was collected and recrystallized from ethanol to give 4.35 mg of 1-benzyl-3-(5'-methoxycarbonyl-2'-furyl)6-methoxyindazole in a 50% yield.(from 4-methoxy phenyl-5'-methoxy carbonyl-2'-furyl ketone)

mp: 108-109° C. MS (%), m/z: 362 ($M^+$). IR (KBr) $\gamma_{max}$: 1710 $cm^{-1}$(C=O). $^1$H-NMR (DMSO-$d_6$, 200 MHz) δ: 3.85(3H, s, —$OCH_3$), 3.88(3H, s, —$COOCH_3$), 5.71 (2H, s,=$NCH_2$—), 6.95(1H,d,J=8.5 Hz,H-5); 7.16(1H,d.J=3.5 Hz,H-3'); 7.24-7.36(6H,m,H-7,phenyl); 7.40 (1H, d, J=3.5 Hz, H-4'), 7.98 (1H, d, J=8.5 Hz, H-4)

A calcium borohydride solution was first prepared by stirring 88.8 mg of anhydrous calcium chloride with 60 mg of sodium borohydride in 20 mL of anhydrous THF for 4 hours. 30 mL of THF solution containing 93.0 mg of 1-benzyl-3-(5'-methoxycarbonyl-2'-furyl)-6-methoxyindazole was added dropwise to the calcium borohydride solution at 30±2° C. The solution thus obtained was heated under reflux for 6 hours, cooled, quenched with crushed ice, placed under reduced pressure to remove THF, and filtered to obtain a solid product. The solid product was purified by column chromatography (silica gel-benzene) to obtain 77.2 mg of Compound 1 in an 88.0% yield.

mp: 109-110° C. MS (%), m/z: 334 ($M^+$). IR (KBr) $\gamma_{max}$: 3400 $cm^{-1}$ (—OH). $^1$H-NMR (DMSO-$d_6$, 200 MHz) δ: 1.90(1H,br,—OH); 3.80(3H,s,6-$OCH_3$); 4.74(2H,d,J=4.9 Hz,—$CH_2O$—); 5.59(2H,s,=$NCH2$—); 6.47(1H,d,J=3.2 Hz,H-4'); 6.59(1H,d,J=2.0 Hz,H-7); 6.84(1H,d,J=3.2 Hz,H-3'); 6.88(1H,dd,J=8.5, 1.5 Hz,H-5); 7.17-7.31 (5H,m,phenyl-H); 7.91(1H,d,J=8.5 Hz,H-4).

EXAMPLE 2

Synthsis of 1-benzyl-3-(5'-hydroxymethyl-2'-furyl)-6-fluoroindazole (Compound 2)

Compound 2 was synthesized by following the procedure as described in Example 1, except that 4-fluorobenzoyl chloride, instead of 4-methoxybenzoyl chloride, was used. The overall yield was 22%.

mp: 110-112° C. MS (%), m/z: 322 ($M^+$). IR (KBr) $\gamma_{max}$: 3450 $cm^{-1}$ (—OH). $^1$H-NMR (DMSO-$d_6$, 200 MHz) δ: 4.49 (2H, br, —$CH_2O$—), 5.45 (1H, br, —OH), 5.88 (1H, s, =$NCH_2$—), 6.48 (1H, d, J=3.2 Hz, H-4'), 6.98 (1H, d, J=3.2 Hz, H-3'), 7.10-7.18 (1H, m, H-7), 7.24-7.36 (5H, m, phenyl-H), 7.70 (1H, dd, J=10.0, 2.0 Hz, C5-H), and 8.15 (1H, dd, J=8.5,5.1 Hz, H-4).

EXAMPLE 3

Synthesis of 1-benzyl-3-(5'-hydroxymethyl-2'-furyl)-6-methylindazole (Compound 3)

Compound 3 was synthesized by following the procedure described in Example 1, except that 4-fluorobenzoyl chloride, instead of 4-methoxybenzoyl chloride, was used. The overall yield was 13%.

mp: 112-114° C. MS (%), m/z: 318 ($M^+$). IR (KBr) $\gamma_{max}$: 3400 $cm^{-1}$ (—OH). $^1$H-NMR (DMSO-$d_6$, 200 MHz) δ: 2.44 (3H, s, —$CH_3$), 4.50 (2H, d. J=5.2 Hz, —$CH_2O$—),5.30(1H, br, —OH), 5.64 (2H, s, =$NCH_2$—), 6.45 (1H, d, J=3.3 Hz, H-4'), 6.07 (1H, d, J=3.3 Hz, H-3'), 7.08 (1H, dd, J=8.3, 1.0 Hz, H-5), 7.19-7.36 (5H, m, phenyl-H), 7.57 (1H, d, J=1.0 Hz, H-7), and 7.98 (1H, dd, J=8.3, 1.0 Hz, H-4).

EXAMPLE 4

Synthesis of 1-benzyl-3-(5'-hydroxymethyl-2'-furyl)-5,6-methylenedioxoindazole (Compound 4)

Compound 4 was synthesized by following the procedure described in Example 1, except that 3,4-methylenedioxobenzoyl chloride, instead of 4-methoxybenzoyl chloride, was used. The overall yield was 29%.

mp: 122-123° C. MS (%), m/z: 348 (M$^+$). IR (KBr) $\gamma_{max}$: 3387 cm$^{-1}$ (—OH). $^1$H-NMR (CDCl$_3$) δ: 2.05 (1H, br, —OH), 4.71 (2H, s, —CH$_2$O—), 5.53 (2H, s, =NCH$_2$—), 5.99 (2H, s, —OCH$_2$O—), 6.43 (1H, d, J=3.3 Hz, H-4'), 6.61 (1H, s, H-7), 6.76 (1H, d, J=3.3 Hz, H-3'), and 7.20-7.31 (6H, m, H-4, phenyl).

EXAMPLE 5

Synthesis of 1-benzyl-3-(5'-methoxymethyl-2'-furyl) indazole (Compound 5)

To 5 mL of dichloromethane solution containing 0.2 g of 1-benzyl-3-(5'-hydroxymethyl-2'-furyl)indazole was added 1.5 mL of 1.0 M BCl$_3$/CH$_2$Cl$_2$ solution at −10±2° C. The solution thus obtained was allowed to react for 4 hours at this temperature. 5 mL of methanol was then added to the solution. The solution was stirred for another 1 hour before it was quenched with ice water to obtain a mixture for extraction with dichloromethane. The extract was neutralized by water wash and dried over anhydrous magnesium sulfate. The solvent was removed under reduced pressure, and the remaining residue was purified by column chromatography (silica gel-benzene) to give 0.15 g of 1-benzyl-3-(5'-methoxymethyl-2'-furyl)indazole in liquid in a 70% yield.

MS (%), m/z: 318 (M$^+$). IR (KBr) $\gamma_{max}$: 1616 cm$^{-1}$ (C—O). $^1$H-NMR (CDCl$_3$, 200 MHz) δ: 3.45 (3H, s, —CH$_2$OCH$_3$), 4.56 (3H, s, —CH$_2$OCH$_3$), 5.29 (2H, s, =NCH$_2$—), 6.52 (1H, d, J=3.3 Hz, H-4'), 6.91 (1H, d, J=3.3 Hz, H-3'), 7.18-7.36 (8H, m, H-5,6,7,phenyl), and 8.12 (1H, dd, J=8.1, 1.1 Hz, H-4).

EXAMPLE 6

Inhibition of PDE 5

Washed human platelets were prepared by the method described in Teng et al. *Biochem. Biophys. Acta.* 1989, 990, 315-320, suspended in 50 mM pH 7.4 Tris-HCl buffer (containing 5 mM MgCl$_2$), and then disrupted by sonication at 4° C. The lysate thus obtained was centrifuged at 39,000×g at 4° C. for 20 minutes to obtain a supernatant which contained PDE 5. Aliquots of the supernatant were taken to prepare PDE 5 solutions in Tris-HCl buffers, each of which contained 10 μM a fused pyrazolyl compound to be tested (i.e., Compound 1, Compound 2, Compound 3, Compound 4, or Compound 5). Each of the PDE 5 solution was first incubated at 37° C. for 5 minutes before 10 μM cGMP was added into it. The cGMP-containing solution was incubated at 37° C. for 30 minutes (during which time cGMP was converted to 5'-GMP by PDE 5), heated to 100° C. for 1 minute, and then cooled to room temperature. *Ophiophagus hannah* snake venom (0.1 mL, 1 mg/mL) was then added to the solution. The solution thus obtained was incubated at 25° C. for 30 minutes to convert 5'-GMP to uncharged guanosine. An ion-exchange resin slurry (1.0 mL; Dowex-1, purchased from Sigma Chemical Co., St. Louis, Mo.) was added to the solution to bind to and remove any remaining cGMP. The cGMP-free solution thus obtained was then centrifuged, and 0.5 mL of the supernatant was taken for quantification of uncharged guanosine in a liquid scintillation counter.

The results show that all of Compounds 1-5 were potent inhibitors of PDE 5. For instance, an unexpectedly low IC$_{50}$ value (3.5 μM) was observed for Compound 1 in inhibiting PDE 5.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating coronary heart disease, hypertension, or impotence, comprising administering to a subject in need thereof an effective amount of a compound having a pyrazolyl core, a first aryl group bonded to 3-C of the pyrazolyl core, and a second aryl group fused at 4-C and 5-C of the pyrazolyl core; wherein the pyrazolyl core is substituted at 1-N, via an alkylene linker, with unsubstituted phenyl; the first aryl group is furyl connected to 3-C of the pyrazolyl core at its 2'-C and substituted at 5'-C with hydroxymethyl; and the second aryl group is phenyl substituted at 5-C and 6-C, together, with methylenedioxo.

2. A method of treating coronary heart disease, hypertension, or impotence, comprising administering to a subject in need thereof an effective amount of a compound, wherein the compound is:

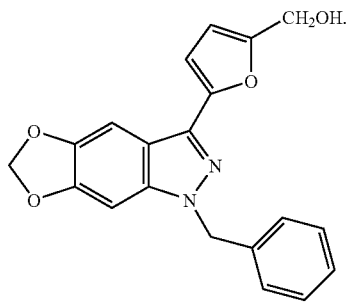

* * * * *